(12) United States Patent
Cosnier et al.

(10) Patent No.: US 10,522,841 B2
(45) Date of Patent: Dec. 31, 2019

(54) ELECTROCHEMICAL REACTOR BLOCK

(71) Applicant: Universite Grenoble Alpes, Saint Martin d'Heres (FR)

(72) Inventors: Serge Cosnier, Grenoble (FR); Raoudha Haddad, Grenoble (FR)

(73) Assignee: UNIVERSITE GRENOBLE ALPES, Saint Martin d'Heres (FR)

( * ) Notice: Subject to any disclaimer, the term of this patent is extended or adjusted under 35 U.S.C. 154(b) by 109 days.

(21) Appl. No.: 15/763,038

(22) PCT Filed: Sep. 14, 2016

(86) PCT No.: PCT/FR2016/052310
§ 371 (c)(1),
(2) Date: Mar. 23, 2018

(87) PCT Pub. No.: WO2017/051095
PCT Pub. Date: Mar. 30, 2017

(65) Prior Publication Data
US 2018/0287166 A1 Oct. 4, 2018

(30) Foreign Application Priority Data
Sep. 25, 2015 (FR) ........................................ 1559069

(51) Int. Cl.
H01M 4/88 (2006.01)
H01M 8/16 (2006.01)
H01M 4/86 (2006.01)
H01M 4/90 (2006.01)
G01N 27/327 (2006.01)
(Continued)

(52) U.S. Cl.
CPC ............. *H01M 4/8875* (2013.01); *C25B 1/02* (2013.01); *C25B 11/0473* (2013.01); *G01N 27/3271* (2013.01); *H01M 4/8626* (2013.01); *H01M 4/9008* (2013.01); *H01M 8/16* (2013.01)

(58) Field of Classification Search
CPC ............ H01M 4/8875; H01M 4/9008; H01M 4/8626; H01M 8/16; G01N 27/3271; C25B 11/0473; C25B 1/02
See application file for complete search history.

(56) References Cited

U.S. PATENT DOCUMENTS

2007/0243449 A1* 10/2007 Sotomura ............ C07D 487/22
429/432
2008/0280751 A1* 11/2008 Harutyunyan ......... B82Y 30/00
502/87
2009/0305089 A1* 12/2009 Minteer ................. C12N 11/00
429/401

FOREIGN PATENT DOCUMENTS

| EP | 2 375 481 A1 | 10/2011 |
| WO | WO 2012/022363 A1 | 2/2012 |
| WO | WO 2012/022921 A1 | 2/2012 |

OTHER PUBLICATIONS

International Search Report for Application No. PCT/FR2016/052310 dated Oct. 27, 2016.
(Continued)

*Primary Examiner* — Stewart A Fraser
(74) *Attorney, Agent, or Firm* — Young & Thompson

(57) ABSTRACT

An electrochemical reactor block including at least two pellets cut out of a flexible conductive film including chains of a linear polymer, carbon nanotubes being bound to each of the chains by pi-pi interaction, a catalyst agent selected from the group including enzymes, metal catalysts, macrocyclic catalysts, and redox mediators being trapped between the pellets.

10 Claims, 2 Drawing Sheets

(51) Int. Cl.
    *C25B 1/02*         (2006.01)
    *C25B 11/04*       (2006.01)

(56) References Cited

OTHER PUBLICATIONS

Hussein et al, Decorated Nanotube Buckypaper as Electrocatalyst for Glucose Fuel Cells. Proceedings IEEE Transducers Conference. Jun. 21, 2009;2254-7.
Written Opinion for Application No. PCT/FR2016/052310 dated Oct. 27, 2016.

* cited by examiner

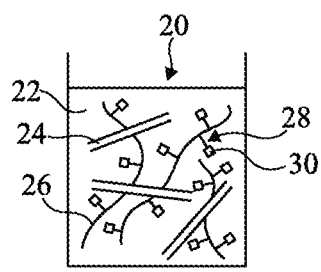 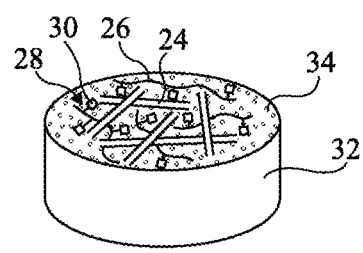 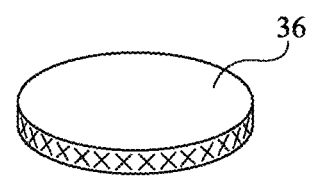
Fig 1A Fig 1B Fig 1C
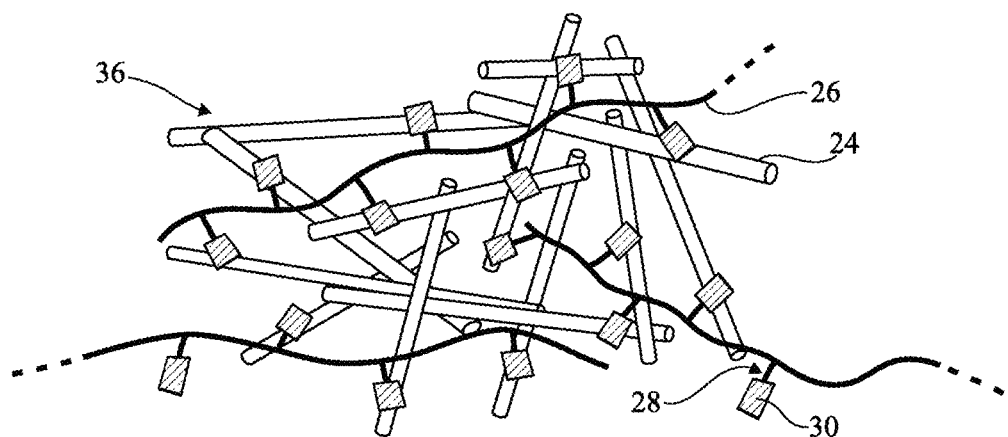
Fig 2

ELECTROCHEMICAL REACTOR BLOCK

This Application is the national stage filing under 35 U.S.C. 371 of International Patent Application Serial No. PCT/FR2016/052310, filed Sep. 14, 2016, which claims priority to French Patent Application No. 15/59069, filed Sep. 25, 2015. The entire contents of these applications are incorporated herein by reference in their entirety to the maximum extent allowable.

BACKGROUND

The present invention relates to a method of manufacturing a block of an electrochemical reactor at the level of which a reaction between catalysts confined in the reactor and compounds present in a liquid medium having the reactor immersed therein is likely to occur. The reaction may for example result in a deformation of the reactor, in the generation of an electric potential, or in the chemical transformation of the compound interacting with the reactor. The reactor may be a bio-reactor.

A bioreactor causing the generation of an electric potential may form a bioelectrode of a biofuel cell or of a biosensor, of sugar-oxygen type, for example, glucose-oxygen.

A bioreactor causing the chemical transformation of a compound interacting with the bioreactor for example forms a glucose killer by, for example, transforming glucose into a compound which will for example be eliminated by the organism where the bioreactor is implanted.

Although the invention and the state of the art are described herein mainly in the case of bioelectrodes, it should be understood that the invention applies to any electrochemical reactor, and not only to a bioreactor implantable in vivo.

DISCUSSION OF THE RELATED ART

Various types of solid bioelectrodes are described in prior art. For example, French patent application filed under number 10/52657 (B10272) describes an electrode pellet obtained by compression of an electrically-conductive material such as graphite, an enzyme, a redox mediator, and possibly an electrically-conductive polymer. The pellet has the shape of a disk having a thickness greater than 0.5 mm and having a diameter greater than 0.5 cm. Although such a pellet can be used as a bioelectrode, its stiffness and its bulk limit its use, particularly in body parts having small volumes, for example, in a blood vessel.

The French patent application filed under number 10/56672 (B10419) describes an electrode pellet obtained by compression of a mixture in solution comprising carbon nanotubes and an enzyme.

Article "Plasma functionalization of bucky paper and its composite with phenylethynyl-terminated polyimide" of Qian Jiang et. al. published in February 2013 in volume 45 of Journal "Composites Part B: Engineering" describes the manufacturing of a conductive film which is a composite of carbon nanotubes and of a polyimide.

These various reactions have disadvantages, and particularly a limited lifetime.

It is desirable to provide an electrochemical reactor overcoming at least some of these disadvantages.

SUMMARY

Thus, an embodiment provides a method of manufacturing an electrochemical reactor block, comprising the steps of:

forming a flexible conductive film comprising chains of a linear polymer, each of which has carbon nanotubes bonded thereto by pi stacking;

cutting pellets from said film; and stacking the pellets and submitting them to a pressure in the order of from 5 to 10 tons per square centimeter in the presence of water and of a catalyst.

According to an embodiment, the step of forming a flexible conductive film comprises the steps of:

preparing a suspension comprising carbon nanotubes and chains of a linear polymer, each of said chains carrying a succession of functional groups, at least some of which comprise pi-conjugated groups; and vacuum filtering the suspension to obtain a film of said chains having the carbon nanotubes bonded thereto by pi stacking.

According to an embodiment, the catalyst is selected from the group comprising enzymes, metal catalysts, macrocyclic catalysts, and redox mediators.

According to an embodiment, the linear polymer is selected from the group comprising polynorbornenes, polyvinyl-pyrrolidone, and sodium polystyrene sulfonate.

According to an embodiment, each of said functional groups comprising a pi-conjugated group is selected from the group comprising porphyrins, phthalocyanine, pyrene, benzene, indole, azulene, phenothiazines, and naphthalene.

According to an embodiment, a distance shorter than the length of the nanotubes separates two successive pi-conjugated groups of a same linear polymer chain.

According to an embodiment, the length of each of said polymer chains is greater than 0.1 μm.

An embodiment provides an electrochemical reactor block comprising at least two pellets cut from a flexible conductive film comprising chains of a linear polymer, each of which has carbon nanotubes bonded thereto by pi stacking, a catalyst selected from the group comprising enzymes, metal catalysts, macrocyclic catalysts, and redox mediators being trapped between the pellets.

According to an embodiment, the electrochemical reaction block forms the cathode of a biofuel cell intended to be immersed in a liquid medium containing a sugar and oxygen, and the catalyst is laccase.

According to an embodiment, the electrochemical reaction block forms the anode of a biofuel cell intended to be immersed in a liquid medium containing a sugar and oxygen, and the catalyst is glucose oxidase.

BRIEF DESCRIPTION OF THE DRAWINGS

The foregoing and other features and advantages will be discussed in detail in the following non-limiting description of specific embodiments in connection with the accompanying drawings, in which:

FIGS. 1A to 1C schematically illustrate steps of an embodiment of a method of manufacturing a flexible conductive film;

FIG. 2 schematically illustrates the structure of a flexible conductive film formed according to the method of FIGS. 1A to 1C;

DETAILED DESCRIPTION

Figure 3:
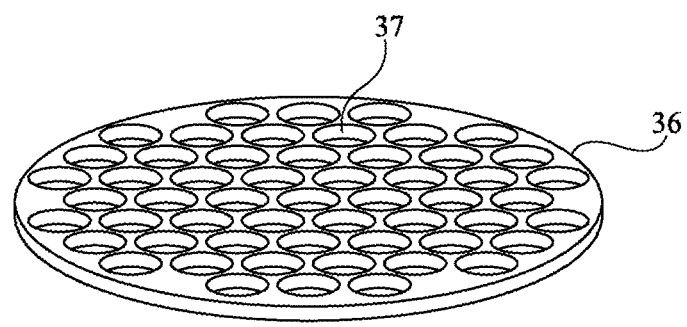
FIG. 3 shows again the film of FIG. 1C.
Figure 4:
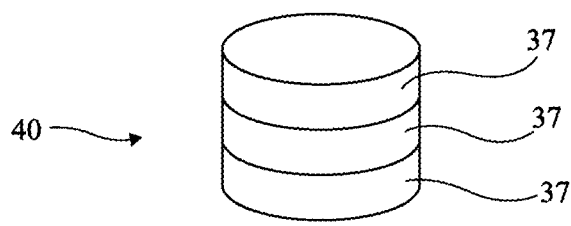
FIG. 4 shows an embodiment of a stack of pellets cut from a film.

The same elements have been designated with the same reference numerals in the different drawings and, further, the various drawings are not to scale. For clarity, only those elements which are useful to the understanding of the described embodiments have been shown and are detailed.

FIGS. 1A to 1C schematically illustrate successive steps of an embodiment of a flexible conductive film.

At the step shown in FIG. 1A, a suspension 20 comprising, in a solvent 22, carbon nanotubes 24 and chains 26 of a linear polymer has been prepared. Preferably, solvent 22 is hydrophobic. The solvent may be selected from the group comprising dimethylformamide (DMF), tetrahydrofuran (THF), N-methyl-2-pyrrolidone (NMP), dimethyl sulfoxide (DMSO), dichloromethane, nitrobenzene, and chloroform. Each chain 26 of the linear polymer carries a succession of functional groups 28 comprising pi-conjugated groups 30. Carbon nanotubes 24 are conductive due to the mobility of the electrons of the pi-conjugated groups of the carbon nanotubes. Thus, a pi-conjugated group 30 of a chain 26 of the linear polymer may bind by pi stacking to a pi-conjugated group of carbon nanotubes 24.

Carbon nanotubes 24 are single-walled or multiwalled nanotubes and may have a length in the range from 100 nm to 5 μm. Each functional group 28 comprising a pi-conjugated group 30 is for example a macrocycle such as porphyrins and phthalocyanine, or an aromatic compound such as pyrene, benzene, indole, azulene, phenothiazines, or naphthalene. The linear polymer may be selected from the group comprising polynorbornenes, polyvinylpyrrolidone (PVP), and sodium polystyrene sulfonate (PSS). Preferably, the distance between two successive pi-conjugated groups 30 of a same chain 26 is shorter than the length of carbon nanotubes 24. This distance is for example in the range from 5 to 50 nm for nanotubes having a length from 200 to 500 nm. The length of chains 26 of the linear polymer is selected to carry a plurality of functional groups 28, for example, at least three functional groups 28, and preferably at least fifty functional groups 28. The length of a chain may be greater than 0.1 μm, preferably greater than 10 μm. The weight of the assembly of carbon nanotubes 24 in suspension 20 is for example from 0.1 to 10 times, preferably from 3 to 6 times, greater than the weight of the assembly of chains 26 of the linear polymer.

At the step illustrated in FIG. 1B, suspension 20 is vacuum-filtered through a membrane 32, for example a PTFE (PolyTetraFluoroEthylene) membrane, comprising pores 34 having a diameter for example in the range from 0.1 to 0.5 μm. Chains 26 of the linear polymer having carbon nanotubes bonded thereto 24 then accumulate in a film at the surface of membrane 32.

As illustrated in FIG. 1C, after the film has been separated from membrane 32, a film 36 comprising carbon nanotubes bonded to the linear polymer chains is obtained. As an example, the thickness of film 36 is in the range from 0.01 to 1 mm. The surface concentration of carbon nanotubes may be 3.4 mg/cm2 and that of the linear polymer chains may be 0.56 mg/cm2.

FIG. 2 is an illustration of chains 26 of linear polymer bonded to carbon nanotubes 24 in film 36. Carbon nanotubes 24 are bonded by pi stacking to pi-conjugated groups 30 of functional groups 28 carried by chains 26 of the linear polymer. A chain 26 carries a plurality of nanotubes 24 and each nanotube may be bonded to a plurality of chains.

Carbon nanotubes 24 of film 36 are in contact with one another, whereby film 36 is electrically conductive. Due to the fact that chains 26 of the linear polymer can deform under the effect of mechanical stress, the obtained film 36 is flexible. In particular, the inventors have observed that such a flexible conductive film can be rolled on itself without breaking.

FIG. 3 shows again the flexible conductive film obtained by the steps previously described in relation with FIGS. 1A to 1C.

It is here provided to cut from this film, which for example has a diameter in the range from approximately 10 to 50 centimeters, and a thickness in the range from approximately 100 to 300 μm, pellets 37. Then, a reactor block 40 is formed by stacking a plurality of these pellets, for example, three in the shown example, and by submitting them to a pressure, for example, in the range from approximately 5 to 10 tons per square centimeter. A highly rigid block is then obtained, provided to have carried out the pressurizing while a few drops of water are inserted between each pellet and between each pellet and the bearing plates of the press. Then, the block easily separates from the press and does not tear or break off in layers. Such a solidity is imputed to the interaction between the pi-pi bonds of the polymer of a pellet and the carbon nanotubes of the adjacent pellet.

The block is functionalized by insertion between the pellets, at the pressurizing, an aqueous solution containing an adapted catalyst.

Thus, the adapted catalyst is trapped between the pellets and a rigid block quite unlikely to break off in layers and having its catalyst immobilized and unlikely to escape into the solution where the block is placed in operation. The compression enables to bond the disks together and, at the same time, this compression and the resulting pi-pi bonds between disks enable to trap the catalysts placed between the disks. A covalent or non-covalent bond may further form between the catalysts and the disks, which further improves the trapping of the catalysts.

The interposed catalysts may be enzymes and/or redox mediators, metal or macrocyclic catalysts or metal nanoparticles, oxides, or metal-organic complexes. All these compounds catalyze a reaction and a reactor has thus been formed and, if there is an electrochemical reaction, it is an electrochemical reactor.

In the case where the catalyst is an enzyme, to improve the trapping thereof, the chains of the linear polymer may carry functional groups capable of bonding to an enzyme in addition to the functional groups comprising pi-conjugated groups. As an example, in the case where the enzyme is conjugated to an avidin, the functional group may be a biotin. As another example, the functional group may be an N-hydroxysuccinimide, which reacts with the amino groups of the enzymes, thus creating a covalent bond between the film and the enzyme. In an alternative embodiment, it may be provided to use bifunctional molecules, each of which carries on the one hand a functional group comprising a pi-conjugated group capable of bonding to an element of the flexible conductive film, and on the other hand a functional group capable of bonding to an enzyme.

Similarly, if the catalyst to be immobilized by trapping it to be associated for its operation with a redox mediator, the film may be specialized with functional groups capable of bonding to a redox mediator. In this case, it is provided for the chains of the linear polymer to carry functional groups capable of bonding to the redox mediator. It may also be provided for the functional groups capable of bonding to the redox mediator to be carried by bifunctional molecules having, on the one hand, a functional group enabling to bond to the redox mediator and, on the other hand, a pi-conjugated group allowing the bonding to the carbon nanotubes, or for the redox mediator to be functionalized by a functional group capable of directly bonding to the carbon nanotubes. As an example, in the case where the redox mediator is toluidine blue, or trimethyl-thionine hydrochloride, it is provided for the film to comprise functional groups comprising activated esters such as N-hydroxy-succinimide reacting with the amino pattern of toluidine blue. The redox mediator may also be viologen, in this case, it is provided to functionalize the viologen with a pi-conjugated group such as a pyrene, the viologen will then be bonded to the film by pi stacking between a carbon nanotube and the pi-conjugated group of the functionalized viologen.

Examples 1 to 4 hereafter are examples of electrochemical reactors comprising catalysts trapped between linear polymer films and carbon nanotubes.

Example 1

The catalyst trapped between the pellets is an enzyme such as a laccase. The system, once immersed in an aqueous solution, for example, in a human or animal body, operates as a cathode and a positive potential appears on a contact formed on an upper pellet.

Example 2

A biofuel cell is formed by using an anode block and a cathode block. The catalyst of the anode block for example comprises glucose oxidase plus a redox mediator and the catalyst of the cathode block for example comprises laccase. This biofuel cell has a low bulk and is implantable in vitro.

Example 3

To form a cell, one may also trap rhodium porphyrin at the level of a first block and cobalt phthalocyanine at the level of a second block. Rhodium porphyrin acts to oxidize glucose and cobalt phthalocyanine acts to reduce oxygen. It should be noted that this reaction only functions when the two blocks are immersed in a solution at high pH, which forms a cell which cannot be implanted in vivo.

Example 4

The catalyst inserted between pellets is formed of platinum nanoparticles. When the system is immersed in an acid medium in an electrolyzer and a current is circulated through the block between a contact formed on an upper pellet and an electrode immersed in the bath of the electrolyzer, the system operates to catalyze the hydrogen generation reaction.

Generally, whatever the catalyst elements used, a good trapping of the catalyst elements and thus a long lifetime of the device will be obtained.

Variations

Specific embodiments have been described. Various variations and modifications will occur to those skilled in the art. In particular, the above-described blocks may be functionalized by other compounds, by other enzymes, and by other redox mediators than those indicated as an example in the present disclosure.

Although blocks comprising a single enzyme and possibly a single redox mediator have been described, more than one enzyme and/or more than one redox mediator may be bonded to a same conductive film.

The blocks described herein may be coated with a semipermeable membrane to let through the reactants of a reaction and stop other heavier elements such as chains of a linear polymer, enzymes, and carbon nanotubes. In the case where the blocks form a bioreactor intended to be implanted in vivo, the membrane is made of a biocompatible material, for example, of chitosan, or of the material designated with trade name Dacron.

The invention claimed is:

1. A method for manufacturing an electrochemical block comprising the steps of:
    forming a flexible conductive film comprising chains of a linear polymer, each of which having carbon nanotubes bonded thereto by pi stacking;
    cutting pellets from said film; and
    stacking the pellets and submitting them to a pressure in the order of from 5 to 10 tons per square centimeter in the presence of water and of a catalyst.

2. The method of claim 1, wherein the step of forming a flexible conductive film comprises the steps of:
    preparing a suspension comprising carbon nanotubes and chains of a linear polymer, each of said chains carrying a succession of functional groups, at least some of which comprise pi-conjugated groups; and
    vacuum filtering the suspension to obtain a film of said chains having the carbon nanotubes bonded thereto by pi stacking.

3. The method of claim 1, wherein the catalyst is selected from the group comprising enzymes, metal catalysts, macrocyclic catalysts, and redox mediators.

4. The method of claim 1, wherein the linear polymer is selected from the group comprising poly-norbornenes, polyvinylpyrrolidone, and sodium polystyrene sulfonate.

5. The method of claim 1, wherein each of said functional groups comprising a pi-conjugated group is selected from the group comprising porphyrins, phthalo-cyanine, pyrene, benzene, indole, azulene, phenothiazines, and naphthalene.

6. The method of claim 1, wherein a distance shorter than the length of the nanotubes separates two successive pi-conjugated groups of a same linear polymer chain.

7. The method of claim 1, wherein the length of each of said polymer chains is greater than 0.1 µm.

8. An electrochemical reactor block comprising at least two pellets cut from a flexible conductive film comprising chains of a linear polymer, each of which has carbon nanotubes bonded thereto by pi stacking, a catalyst selected from the group comprising enzymes, metal catalysts, macrocyclic catalysts, and redox mediators being trapped between the pellets.

9. The electrochemical reactor block of claim 8, forming the cathode of a biofuel cell intended to be immersed in a liquid medium containing a sugar and oxygen, wherein said catalyst is laccase.

10. The electrochemical reactor block of claim 8, forming the anode of a biofuel cell intended to be immersed in a liquid medium containing a sugar and oxygen, wherein said catalyst is glucose oxidase.

* * * * *